United States Patent [19]
Bennett

[11] Patent Number: 5,814,619
[45] Date of Patent: Sep. 29, 1998

[54] OLIGONUCLEOTIDE INHIBITION OF P120

[75] Inventor: Clarence Frank Bennett, Carlsbad, Calif.

[73] Assignee: Isis Pharmacuticals, Inc., Carlsbad, Calif.

[21] Appl. No.: 225,444

[22] Filed: Apr. 8, 1994

[51] Int. Cl.[6] .................................................. A61K 31/70
[52] U.S. Cl. ........................................... 514/44; 536/23.1
[58] Field of Search ................................ 435/6; 536/23.1; 514/44

[56] References Cited

U.S. PATENT DOCUMENTS

| 5,087,617 | 2/1992 | Smith | 514/44 |
| 5,098,890 | 3/1992 | Gewirtz et al. | 514/44 |
| 5,166,195 | 11/1992 | Ecker | 514/44 |

FOREIGN PATENT DOCUMENTS

WO 93/17125   2/1993   WIPO .

OTHER PUBLICATIONS

RNA Structure from A To Z, Tinoco, Jr., et al.,*Cold Spring Harbor Symposia on Quantitative Biology*, vol. LII, pp. 135–146 (1987).
RNA Secondary Structure is an Integral Part of the in vitro Mechanism of Attenuation in Simian Virus 40, Resnekov, et al., *The Journal of Biological Chemistry*, 264:9953 (1989).
CUUCGG Hairpins: Extraordinarily Stable RNA Secondary Structures Associated with Various Biochemical Processes, Tuerk, et al, *Proc. Natl. acad. Sci. USA*, 85:1364 (1988).
Busch, "The Final Common Pathway of Cancer: Presidetnial Address", *Cancer Res.* 50: 4830–4838 (1990).
Davis et al., "Nucleolar Antigen Found in Several Human Tumors But Not in the Nontumor Tissues Studied", *Proc. Natl. Acad. Sci. U. S. A.* 76: 892–896 (1979).
Fonagy et al., "Antisense–Mediated Specific Inhibition of P120 Protein Expression Prevents $G_1$–to S–Phase Transition", *Cancer Res.* 52:5250 (1992).
Freeman et al., "Identification and Characterization of a Human Proliferation–associated Nucleolar Antigen with a Molecular Weight of 120,000 Expressed in Early $G_1$ Phase", *Cancer Research*. 48: 1244–1251 (1988).
Freeman et al., "Prognostic Significance of Proliferation Associated Nucleolar Antigen P120 in Human Breast Carcinoma", *Cancer Research* 51: 1973–1978 (1991).
Freeman and Bondada, "Inhibiton of Cell Proliferation by Microinjection of Antibodies to Nucleolar Antigen P120", *Am. Assoc. Cancer Res.* 31:261 (1990).
Larson et al., "Genomic Structure of the Human Proliferating Cell Nucleolar Protein P120", *Cancer Comm.* 2: 63–71 (1990).
Ochs et al., "Intranucleolar Localization of Human Proliferating Cell Nucleolar Antigen p120", *Cancer Res.* 48: 6523–6529 (1988).
Saijo et al., "The Effect of Antisense p120 Construct on p120 Expression and Cell Proliferation in Human Breast Cancer MCF–7 Cells", *Cancer Letters* 68: 95–104 (1993).
Wahl et al, Methods Enzymol. 152:399 (1987).
Larson et al, Entrez, Release 3.0, Feb. 15, 1993.
Perlaky et al, Cancer Res. 52: 428 (1992).

*Primary Examiner*—James Martinell
*Attorney, Agent, or Firm*—Woodcock Washburn Kurtz Mackiewicz & Norris LLP

[57] ABSTRACT

Certain oligonucleotides capable of inhibiting the production of p120, a cell proliferation-associated nucleolar protein, are provided. Oligonucleotides designed to be hybridizable with nucleic acids encoding nucleolar proteins are believed to be therapeutically useful. Certain of such oligonucleotides, hybridizable to MRNA encoding p120, were made and found to inhibit the synthesis of p120. The oligonucleotides of the invention are useful for the treatment of diseases characterized by hyperproliferation of cells. Methods of treatment and diagnosis of such diseases using these oligonucleotides are also provided.

2 Claims, 1 Drawing Sheet

OLIGONUCLEOTIDE INHIBITION OF P120

FIELD OF THE INVENTION

This invention relates to oligonucleotides which inhibit the production of a protein, p120, which is synthesized in proliferating cells. Certain oligonucleotides designed to hybridize to the mRNA encoding p120 are provided to effect this goals. These oligonucleotides have been found to lead to inhibition of the synthesis of p120. This invention also relates to diagnostics, research reagents, and therapies for disease states which respond to inhibition of the synthesis of p120.

BACKGROUND OF THE INVENTION

Malignant neoplasms have several characteristics which distinguish them from benign tumors and normal cells. These features include uncontrolled cell growth, invasiveness and metastasis. Malignant tumors may be differentiated from benign tumors or normal cells by morphological characteristics including anaplastic cells, increased mitotic index, abnormal mitotic cells, variable size and shape, increased nuclear to cytoplasmic ratio, and large, prominent nucleoli. Much research has been focused on the biochemical and genetic characterization of malignant cells attempting to identify differences responsible for these phenotypic changes. Such studies have led to the identification of so-called "oncogenes" which, if overexpressed or mutated, promote malignant transformation of cells.

Current agents which affect cellular proliferation are nonspecific cytotoxic agents such as DNA alkylating agents, DNA intercalators or microtubule depolymerizing agents. These agents all suffer from severe toxicities and lack of specificity towards the malignant cell. Thus, there is a long-felt need for molecules which effectively inhibit proliferation of malignant cells without such drawbacks. Oligonucleotides designed to hybridize with nucleic acids encoding proliferation-associated proteins represent a novel approach to selective inhibition of gene expression, in particular expression of p120.

SUMMARY OF THE INVENTION

Figure 1:
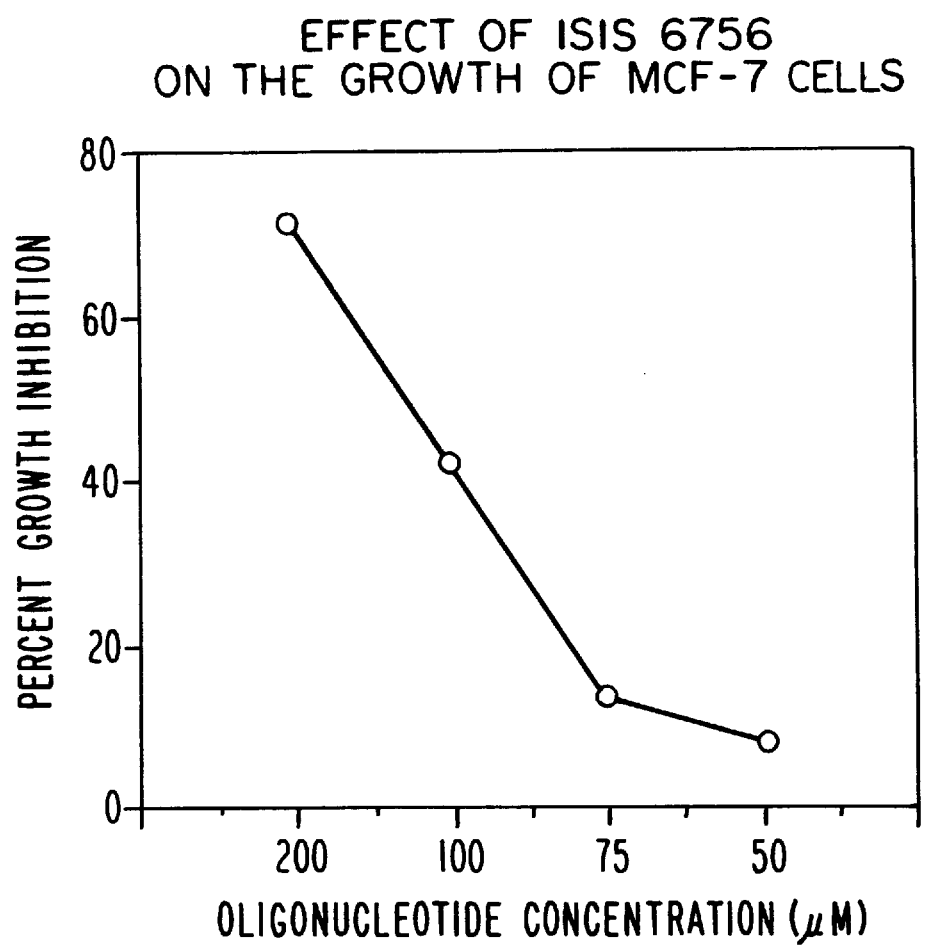
FIG. 1 is a line graph showing the effect of ISIS 6756 on the growth of MCF-7 human breast cancer cells. Growth inhibition is expressed as percent of control (cells treated with nonsense oligonucleotide).

In accordance with the present invention, oligonucleotides are provided which are specifically hybridizable with nucleic acids encoding the proliferation-associated protein p120. The oligonucleotides are useful for inhibiting the production of p120 and for detection and diagnosis. It is believed that inhibition of p120 expression is useful for the treatment of inflammatory and hyperproliferative diseases.

Methods of inhibiting cell proliferation with an effective amount of an oligonucleotide hybridizable with nucleic acids encoding p120 are provided. Methods of diagnosing hyperproliferative diseases are also provided.

DETAILED DESCRIPTION OF THE INVENTION

It has been found that certain nucleolar proteins are implicated in hyperproliferative disease, especially certain cancers. The pleomorphism and hyperactivity of nucleoli characteristic of malignant cells prompted studies attempting to identify differences between normal and malignant nucleoli. Early experiments attempting to identify nucleolar proteins which were expressed only in malignant cells, utilized rabbits immunized with nucleoli isolated from malignant cells and preabsorption of the sera with nucleolar extracts isolated from normal cells. Busch, et al., *Cancer Res.* 34: 2362–2367 (1974); Busch et al., *Proc. Soc. Exp. Biol. Med.*, 160: 185–191 (1979); Davis et al., *Proc. Natl. Acad. Sci. U.S.A.*, 76: 892–896 (1979); Busch et al., *Cancer Res.*, 39: 3024–3030 (1979). These studies resulted in the identification of rabbit antisera which reacted with a broad range of human cancers but not normal human tissues. The major problem of this type of an approach was the difficulties associated with rabbit antibodies in terms of reproducibility between animals, variable titer and polyclonal nature of the antibodies.

Based upon the initial positive results with polyclonal rabbit antiserum, efforts were made to purify and characterize tumor specific nucleolar proteins. Proteins which were not found in the normal tissues examined were purified from either rat or human tumors. Chan et al., *Transplant. Proc.*, 8: 1955–1957 (1981); Chan et al., *Cancer Res.*, 40: 3194–3201 (1980);

Chan et al., *J. Cancer Res. Clin. Oncol.*, 103: 7–16 (1982);

Takahashi et al., *Cancer Res. Clin. Oncol.*, 105: 67–75 (1983). Two-dimensional gel analysis of nucleolar proteins isolated from malignant and normal tissues also identified several proteins unique to malignant cells. Spohn et al. *Cancer Invest.* 3: 307–320 (1985).

Because of the lack of reproducibility of polyclonal antisera, monoclonal antibodies to human tumor nucleolar antigens were developed. These studies resulted in the identification of several proteins associated with proliferating cells but undetectable in normal quiescent cells. These monoclonal antibodies were demonstrated to react with a 145 kDa protein, a 40 kDa protein and a 120 kDa protein. Freeman et al., *Cancer Res.*, 46: 3593–3598 (1986); Chatterjee et al., *Cancer Res.*, 47: 1123–1129 (1987); Freeman et al., *Cancer Res.*, 48: 1244–1251 (1988). These antigens were found to be expressed in a similar manner as the cyclins during the G1 to S phase of the cell cycle as shown by Matthews et al., *Nature*, 3009: 374–376 (1983).

The 120 kDa nucleolar antigen (p120) was of particular interest in that it was detected in a wide variety of human malignancies but not in most normal tissues. Further studies suggested that p120 may be a prognostic marker in breast cancer in that patients with p120-negative tumors had a good prognosis while patients with p120-positive tumors had a poor prognosis. Freeman et al., *Cancer Res.*, 51: 1973–1978 (1991). Thus abnormal expression of p120 appears to correlate with abnormal cell proliferation The p120 antigen is apparently related to the proliferative state of the cell and nucleolar hyper-reactivity. In support of this conclusion was the finding that microinjection of p120 antibodies into tumor cells decreases their proliferative rate and induces a compaction of the nucleolus. Freeman and Bondada, *Am. Assoc. Cancer Res.*, 31: 261 (1990). p120 has, however, also been identified in small amounts in normal proliferating tissues as shown by Freeman et al., *Cancer Res.*, 48: 1244–1251 (1988).

Multiple overlapping cDNA clones for p120 were isolated and sequenced; the genomic DNA sequence was also determined. Busch et al., *Cancer Res.*, 50: 4830–4838 (1990); Fonagy et al., *Cancer Commun.*, 1: 243–245 (1989); Larson et al., *Cancer Commun.,* 2: 63–71 (1990). Four major domains were identified in the p120 protein, a basic amino terminal domain, followed by an acidic domain, a hydrophobic domain, and a domain rich in proline and cysteine residues. A search of the computer data bases did not reveal any significant homology between p120 and other known proteins other than an acidic domain shared by other nucleolar proteins. The gene for p120 was subsequently demonstrated to be 12 kb in length, composed of 15 exons and 14 introns. Larson et al., *Cancer Comm.,* 2: 63–71 (1990).

The function of p120 in proliferating cells is currently unknown. The protein was identified as a component of the nucleolar matrix, associated with a network of 20 to 30 nm beaded fibrils. Ochs et al., *Cancer Res.,* 48: 6523–6529 (1988). Roles suggested for p120 include transcription of ribosomal RNA or replication of ribosomal DNA or a structural role in the nucleolar matrix.

Certain vector constructs designed to be antisense to all or a portion of a gene coding for a nucleolar protein, p120, have been found to inhibit the growth of human breast carcinoma cells in culture. saijo, et al., *Cancer Letters,* 68: 95–104 (1993); WO Application 93/15743. An antisense pentadecadeoxyribonucleotide complementary to a splice junction site of p120 mRNA has been used to inhibit expression of p120 and the mitogen-induced proliferation of human lymphocytes. Fonagy et al., *Cancer Res.*52: 1–7 (1993). This 15mer and certain other antisense oligonucleotides targeted to p120 have been used to inhibit the growth of human cancer cells and transplanted human amelanotic melanoma tumor cells in nude mice. WO 93/17125 (Busch, Bennett et al.).

It is believed that breast cancer and other hyperproliferative diseases characterized by abnormal p120 expression may be similarly treated with the additional novel oligonucleotides of the present invention, which are specifically hybridizable with nucleic acids encoding p120.

Oligonucleotides have recently become accepted as therapeutic moieties in the treatment of disease states in animals and man. Workers in the field have now identified antisense, triplex and other oligonucleotide therapeutic compositions which are capable of modulating expression of genes implicated in viral, fungal and metabolic diseases.

For example, U.S. Pat. No. 5,098,890 is directed to antisense oligonucleotide therapies for certain cancerous conditions. U.S. Pat. No. 5,135,917, issued Aug. 4, 1992, provides antisense oligonucleotides that inhibit human interleukin-l receptor expression. U.S. Pat. No. 5,087,617, issued Feb. 11, 1992, provides methods for treating cancer patients with antisense oligonucleotides. U.S. Pat. No. 5,166,195 issued Nov. 24, 1992 provides oligonucleotide inhibitors of HIV. U.S. Pat. No. 5,004,810, issued Apr. 2, 1991, provides oligomers capable of hybridizing to herpes simplex virus Vmw65 mRNA and inhibiting replication. U.S. Pat. No. 5,194,428, issued Mar. 16, 1993, provides antisense oligonucleotides having antiviral activity against influenzavirus. U.S. Pat. No. 4,806,463, issued Feb. 21, 1989, provides antisense oligonucleotides and methods using them to inhibit HTLV-III replication. Antisense oligonucleotides have been safely administered to humans and several clinical trials are presently underway. It is, thus, established that oligonucleotides can be useful therapeutic instrumentalities and can be configured to be useful in treatment regimes for treatment of cells and animals, especially humans.

For therapeutics, methods of inhibiting cell proliferation are provided, using oligonucleotides in accordance with this invention. Persons of ordinary skill can easily determine optimum dosages, dosing methodologies and repetition rates. Such treatment is generally continued until either a cure is effected or a diminution in the disease state is achieved. Long term treatment is likely for some diseases.

The formulation of therapeutic compositions and their subsequent administration is believed to be within the skill in the art. In general, for therapeutics, a patient suspected of needing such therapy is given an oligonucleotide in accordance with the invention, commonly in a pharmaceutically acceptable carrier, in amounts and for periods which will vary depending upon the nature of the particular disease, its severity and the patient's overall condition. The pharmaceutical compositions of this invention may be administered in a number of ways depending upon whether local or systemic treatment is desired, and upon the area to be treated. Administration may be topical (including ophthalmic, vaginal, rectal, intranasal), oral, or parenteral, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The present invention is also suitable for diagnosing hyperproliferative states in tissue or other samples from patients suspected of having a hyperproliferative disease. Thus, the ability of the oligonucleotides of the present invention to hybridize with nucleic acids encoding p120 may be employed to diagnose such states. A number of assays may be formulated employing the present invention, which assays will commonly comprise contacting a tissue sample with an oligonucleotide of the invention under conditions selected to permit hybridization, detection and, usually, quantitation of such inhibition.

The oligonucleotides of this invention may also be used for research purposes. Thus, the specific hybridization exhibited by the oligonucleotides may be used for assays, purifications, cellular or subcellular preparations and in other methodologies which may be appreciated by persons of ordinary skill in the art.

The present invention employs oligonucleotides designed to be specifically hybridizable with nucleic acids encoding p120. This relationship between an oligonucleotide and its complementary nucleic acid target is commonly referred to as "antisense." "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "substantially complementary" are terms which indicate a sufficient degree of complementarity such that stable and specific binding occurs between the target and the oligonucleotide or analog. It is understood that an oligonucleotide need not be 100% complementary to its target nucleic acid sequence to be specifically hybridizable. An oligonucleotide is specifically hybridizable when binding of the oligonucleotide to the target interferes with the normal function of the messenger RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted.

In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J.E. and Weller, D. D., U.S. Pat. No. 5,034,506. In other preferred embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Other preferred oligonucleotides may contain sugar moieties comprising one of the following at the 2' position: OH, SH, $SCH_3$, F, OCN, $O(CH_2)_n NH_2$ or $O(CH_2)_{nCH3}$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N—alkyl; O—, S—, or N—alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. oligonucleotides may also have sugar mimetics such as cyclobutyls in place of the pentofuranosyl group. Oligonucleotides may also include species which include at least some modified base forms. Thus, purines and pyrimidines other than those normally found in nature may be employed. "Universal" bases such as inosine may also be included.

Such oligonucleotides are best described as being functionally interchangeable with natural oligonucleotides (or synthesized oligonucleotides along natural lines), but which have one or more differences from natural structure. All such oligonucleotides are comprehended by this invention so long as they function effectively to hybridize with the selected RNA. The oligonucleotides in accordance with this invention comprise from about 12 to about 50 nucleic acid base units. It is preferred that such oligonucleotides comprise from about 12 to 25 nucleic acid base units. The terms "nucleoside" and "nucleic acid base unit" are used interchangeably and refer to a base-sugar combination suitably bound to an adjacent nucleic acid base unit through phosphodiester or other bonds. In the context of this invention, the base and sugar portions of the nucleoside may be modified as hereinbefore described.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

In the context of this invention, the terms "mRNA" and "messenger RNA" include not only the region ("coding region") of the ribonucleic acid which contains the information to encode a protein using the three letter genetic code, but also associated ribonucleotides which form regions known to those skilled in the art as the 5'-untranslated region, the 3'-untranslated region, the 5' cap region, intron regions and intron/exon or splice junction ribonucleotides. Antisense oligonucleotides can be targeted to any of these regions, or portions thereof, in order to achieve the desired interference with mRNA function. The functions of messenger RNA to be interfered with include all vital functions such as translocation of the RNA to the site for protein translation, translation of protein from the RNA, maturation of the RNA and possibly even independent catalytic activity which may be engaged in by the RNA. The overall effect of such interference with the RNA function is to cause interference with expression of p120.

It has now been found that certain oligonucleotides specifically hybridizable with portions of the mRNA encoding the nucleolar protein p120 are particularly useful for interfering with expression of p120 and for inhibiting cell hyperproliferation.

The following oligonucleotides were synthesized:

TABLE 1

Oligonucleotides targeted to p120 mRNA
(P=S indicates phosphorothioate backbone;
2'OMe indicates O—methyl at each 2' position)

| Oligo # | Target region | Sequence | | | | | | Modif. | SEQ ID NO: |
|---|---|---|---|---|---|---|---|---|---|
| 6739 | Splice jct. | GUC | AAA | GCC | CCC | CAC | CAC | P=S, 2'OMe | 1 |
| 6749 | Splice jct. | GTC | AAA | GCC | CCC | CAC | CAC | P=S | 2 |
| 6748 | 5' UTR | AGA | AGG | TGG | CGT | CGC | GCG | TG | P=S | 3 |
| 6755 | 3' UTR | GCG | GCA | AAG | GCA | GCA | CCC | AG | P=S | 4 |
| 6756 | AUG region | GCG | CCC | CAT | GGT | ACT | GTG | GC | P=S | 5 |
| 7433 | nonsense | ACG | TCC | TGC | AGT | CGC | GTG | CG | P=S | 6 |

The nonsense oligonucleotide ISIS 7433 is a negative control.

The oligonucleotides of Table 1 were tested in the mitogen-stimulated lymphocyteproliferation assay. Peripheral blood lymphocytes isolated from normal donors were treated with the mitogen phytohemagglutinin (PHA) and incubated for 20 hours. Oligonucleotides were added 4 hours prior to PHA stimulation and cell proliferation was assayed (by measuring radioactive nucleoside incorporation) to determine the effect of each oligonucleotide on the proliferation of the lymphocytes in response to PHA.

The results are shown in Table 2, expressed as percent of proliferation of control-treated cells.

TABLE 2

Percent Inhibition of Lymphocyte Proliferation by
Antisense Oligonucleotides Targeted to p120

| | Oligonucleotide dose: | | | |
|---|---|---|---|---|
| Oligo # | 25 µM | 50 µM | 100 µM | 200 µM |
| 6739 | 42 | 52 | 34 | 34 |
| 6749 | −20 | 29 | 23 | 14 |
| 6748 | 49 | 59 | 58 | 73 |
| 6755 | −13 | 46 | 48 | 74 |
| 6756 | 65 | 61 | 71 | 94 |

In these experiments, oligonucleotides showing 50% or greater inhibition of proliferation at any concentration were considered active and are preferred. Thus, ISIS 6739, ISIS 6748, ISIS 6755 and ISIS 6756 are preferred, with ISIS 6756 being most preferred.

The effect of ISIS 6756 on the growth of MCF-7 human breast cancer cells was determined. Cells were treated with ous concentrations of ISIS 6756 and a nonsense control oligonucleotide. After 24 hours an MTT assay was done to determine cell numbers (i.e., extent of proliferation). The inhibition of growth of MCF-7 cancer cells by ISIS 6756 was found to be dose-dependent, as shown in FIG. 1.

The effect of oligonucleotide treatment on MCF-7 cells evaluated over time. MCF-7 cells were treated with ISIS and a nonsense control oligonucleotide. Oligonucleotide concentration was 100 µM and cell numbers were determined by MTT assay on days 2,3,4 and 7. By day 7 most of the cells treated with ISIS 6756 were dead whereas the nonsense control- treated cells showed rapid exponential growth.

The invention is further illustrated by the following examples which are meant to be illustrations only and are not intended to limit the present invention to specific embodiments.

EXAMPLE 1

Synthesis and Characterization of Oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl phosphoramidites were purchased from Applied Biosystems (Foster City, Calif.). For phosphorothioate oligonucleotides, the standard oxidation bottle was replaced by a 0.2 M solution of H1,2-benzodithiole-3-one 1,1-dioxide in acetonitrile for the stepwise thiation of the phosphite linkages. The thiation cycle wait step was increased to 68 seconds and was followed by the capping step. 2' -O-methyl phosphorothioate oligonucleotides were synthesized using 2' -O-methyl β- cyanoethyl-diisopropylphosphoramidites (Chemgenes, Needham MA) and the standard cycle for unmodified oligonucleotides, except the wait step after pulse delivery of tetrazole and base was increased to 360 seconds. The 3' -base used to start the synthesis was a 2' -deoxyribonucleotide. After cleavage from the controlled pore glass column (Applied Biosystems) and deblocking in concentrated ammonium hydroxide at 55° C for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and their phosphorothioate analogs were judged from electrophoresis to be greater than 80% full length material.

EXAMPLE 2

Mitogen-stimulated lymphocyte proliferation assay

Mitogen-induced proliferation of cells, and its inhibition by oligonucleotides, was measured by [$^3$H]thymidine incorporation into the DNA of lymphocytes. Peripheral blood lymphocytes were isolated from normal donors by Ficoll-Paque (Pharmacia, Piscataway, N.J.) density centrifugation. Cell concentration was 1×10$^6$ ml in RPMI medium containing 10% heat-inactivated fetal bovine serum. The mitogen phytohemagglutinin (PHA) was added to a final concentration of 2 µg/ml. Aliquots of 100 µl of cell concentrate were plated into 12 wells of a 96-well microtiter plate and incubated for 20 hours. Cells were treated with 50 Al each of oligonucleotide and PHA. Oligonucleotides were added 4 hours prior to PHA stimulation. An additional 50 µl of medium containing 1 µCi of [$^3$H]thymidine (1 mCi/ml) or [$^3$H]uridine (1 mCi/ml) (ICN Biomedicals, Inc., Costa Mesa, Calif.) was added to each well. After 4 hours incubation at 37° with radioactive nucleotide in a 5% $CO_2$ atmosphere, cells were harvested onto glass fiber filters with 6 washes of running distilled water using a cell harvester (Cambridge Technology Inc., Watertown, Mass.). Filters were placed into scintillation fluid and radioactivity was counted in a liquid scintillation counter.

EXAMPLE 3

Oligonucleotide treatment of MCF-7 breast cancer cell lines

Human breast cancer MCF-7 cells were obtained from the American Type Culture Collection (ATCC) and grown in DMEM with 10% fetal bovine serum. Cells were treated with various 25 concentrations of ISIS 6756 and a nonsense control oligonucleotide. After 24 hours an MTT assay was done to determine extent of proliferation. This method measures cell viability and is based on the reduction of the tetrazolium salt, 3-(4,5-dimethyl-thiazol-2-yl)-2,5-diphenyl tetrazolium bromide (MTT) to MTT formazan by mitochondrial enzymes of viable cells. Mosmann, T., J. Immunol. Methods. 65:55 (1983). Cells are treated with MTT followed by SDS to dissolve the crystals of MTT formazan. The blue color of the MTT formazan is measured spectrophotometrically at 570 nm on an automated plate reader. Viability is determined by comparing the absorbance of treated cells with the mean absorbance of the cell control (nonsense oligonucleotide-treated) cultures and expressed as percent of control.

The effect of oligonucleotide treatment on MCF-7 cells was also evaluated over time. MCF-7 cells were treated with ISIS 6756 and a nonsense control oligonucleotide. Oligonucleotide concentration was 100 $\mu$MM and cell numbers were determined by MTT assay on days 2,3,4 and 7.

What is claimed is:

1. A method of inhibiting the synthesis of p120 comprising contacting cells suspected of having abnormal p120 expression with an amount effective to inhibit p120 of an oligonucleotide which hybridizes with mRNA encoding p120, said oligonucleotide consisting of a nucleotide sequence selected from the group consisting of SEQ ID NO: 1, SEQ ID NO: 3, SEQ ID NO: 4 and SEQ ID NO: 5.

2. The method of claim 1 wherein at least one of the linking groups between nucleic acid base units is a phosphorothioate moiety.

* * * * *

UNITED STATES PATENT AND TRADEMARK OFFICE
CERTIFICATE OF CORRECTION

PATENT NO. : 5,814,619
DATED : September 29, 1998
INVENTOR(S) : Bennett

It is certified that error appears in the above-identified patent and that said Letters Patent is hereby corrected as shown below:

Column 3, line 21, please delete "saijo" and insert therefor --Sajko--;
Column 8, line 51, please delete "A1" and insert therefor --$\mu$1--.

Signed and Sealed this

Sixteenth Day of November, 1999

Attest:

Q. TODD DICKINSON

Attesting Officer    Acting Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 18
        ( B ) TYPE: Nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 1:

GUCAAAGCCC CCCACCAC 18

( 2 ) INFORMATION FOR SEQ ID NO: 2:

( i ) SEQUENCE CHARACTERISTICS:
        ( A ) LENGTH: 18
        ( B ) TYPE: Nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 2:

GTCAAAGCCC CCCACCAC 18

( 2 ) INFORMATION FOR SEQ ID NO: 3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 3:

AGAAGGTGGC GTCGCGCGTG 20

( 2 ) INFORMATION FOR SEQ ID NO: 4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 4:

GCGGCAAAGG CAGCACCCAG 20

(2) INFORMATION FOR SEQ ID NO: 5:

(i) SEQUENCE CHARACTERISTICS:
      (A) LENGTH: 20
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 5:

GCGCCCCATG GTACTGTGGC 20

(2) INFORMATION FOR SEQ ID NO: 6:

(i) SEQUENCE CHARACTERISTICS:
      (A) LENGTH: 20
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 6:

ACGTCCTGCA GTCGCGTGCG 20